United States Patent
Felder

(10) Patent No.: US 8,865,733 B2
(45) Date of Patent: Oct. 21, 2014

(54) MEDICATION AND TREATMENT FOR DISEASE

(75) Inventor: Mitchell S. Felder, Hermitage, PA (US)

(73) Assignee: Altman Enterprises, LLC, El Paso, TX (US)

(*) Notice: Subject to any disclaimer, the term of this patent is extended or adjusted under 35 U.S.C. 154(b) by 217 days.

(21) Appl. No.: 13/128,177

(22) PCT Filed: Oct. 31, 2009

(86) PCT No.: PCT/US2009/062895
§ 371 (c)(1),
(2), (4) Date: May 6, 2011

(87) PCT Pub. No.: WO2010/053854
PCT Pub. Date: May 14, 2010

(65) Prior Publication Data
US 2011/0217278 A1   Sep. 8, 2011

Related U.S. Application Data

(60) Provisional application No. 61/111,830, filed on Nov. 6, 2008, provisional application No. 61/148,431, filed on Jan. 30, 2009.

(51) Int. Cl.
| | | |
|---|---|---|
| A61K 31/44 | (2006.01) | |
| A61K 31/12 | (2006.01) | |
| A61K 31/70 | (2006.01) | |
| A61K 31/435 | (2006.01) | |
| A61K 31/135 | (2006.01) | |
| A61K 31/4415 | (2006.01) | |
| A61K 31/585 | (2006.01) | |
| A61K 31/122 | (2006.01) | |
| A61K 31/714 | (2006.01) | |

(52) U.S. Cl.
CPC ........... *A61K 31/122* (2013.01); *A61K 31/4415* (2013.01); *A61K 31/585* (2013.01); *A61K 31/714* (2013.01)

USPC ............ 514/282; 514/689; 514/52; 514/277; 514/654

(58) Field of Classification Search
CPC . A61K 31/485; A61K 31/122; A61K 31/714; A61K 31/4415; A61K 31/137
See application file for complete search history.

(56) References Cited

U.S. PATENT DOCUMENTS

| 5,888,980 | A * | 3/1999 | Ripka ............................ 514/9.7 |
| 6,503,506 | B1 * | 1/2003 | Germano ..................... 424/94.3 |
| 2004/0116351 | A1 | 6/2004 | Halevie-Goldman | |
| 2007/0259939 | A1 | 11/2007 | Stebbing | |

OTHER PUBLICATIONS

Maggini et al. "Selected Vitamins and Trace Elements Support Immune Function by Strengthening Epithelial Barriers and Cellular and Humoral Immune Responses". British Journal of Nutrition. 2007; 98(Suppl.1):S29-S35.*
Agrawal YP. "Low Dose Naltrexone Therapy in Multiple Sclerosis". Medical Hypotheses. 2005; 64:721-724.*

* cited by examiner

*Primary Examiner* — Leslie A. Royds Draper

(57) ABSTRACT

A treatment is described for diseases with symptoms that can include fatigue, muscle aches and spasms, weakness, demylenation, and nerve pain. Diseases can include fibromyalgia, depression, and auto-immune and immuno-suppressive diseases, such as MS. The treatment comprises about 1-10 mg naltrexone, at least about 20 μg vitamin B12, at least about 5 mg vitamin B6, at least about 2 mg coenzyme Q, and preferably at least one ancillary medication selected from the group consisting of diazepam, cyclcobenzaprine, clonazepam, alprazolam, 9-tetrahydrocannibinol, fumarate, caffeine, and combinations thereof. The treatment can be administered orally, and can decrease mental and physical symptoms such as, for example, fatigue, gait problems, visual dysfunction, and pain while improving cognitive skills.

1 Claim, No Drawings

MEDICATION AND TREATMENT FOR DISEASE

FIELD OF THE INVENTION

The present invention relates to a treatment for diseases, such as fibromyalgia, depression, and auto-immune and immuno-suppressive diseases, including MS.

BACKGROUND OF THE INVENTION

Various diseases can include symptoms such as fatigue, muscle aches, muscle spasms, tingling of the skin, weakness, demyelenation (loss of myelin), and nerve pain. Examples of such diseases can include fibromyalgia, depression, and auto-immune and immuno-suppressive diseases, such as MS.

These diseases, particularly immune related and inflammatory diseases, are the manifestation of complex, often multiple interconnected biological pathways. Normally, such pathways respond to insult or injury, initiate repair from insult or injury, and defend against foreign organisms using innate and acquired defenses. Disease or pathology occurs when these normal pathways malfunction and cause additional insult or injury either because of the intensity of the response, abnormal regulation, excessive stimulation, and/or an autoimmune response. Autoimmune related causes have been treated by suppressing the immune response, for example by using neutralizing antibodies or molecules, such as proteins, that inhibit immune stimulatory activity Multiple sclerosis (MS) is an example of an autoimmune related inflammatory disease. MS is a degenerative neurological disease that affects the central nervous system, and is associated with formation of neuronal plaques and impaired neuronal conduction due to demyelination. Although lacking any known cure, therapeutic intervention can occur by either antagonism of a detrimental process/pathway or stimulation of a beneficial process/pathway.

An effective treatment for MS patients would include improved mental function and physical stamina and facility. Preferably, the treatment would be easily administered, such as by ingestion rather than injection.

SUMMARY OF THE INVENTION

The present invention describes a medication and treatment for diseases, such as fibromyalgia, depression, and auto-immune and immuno-suppressive diseases, including MS. Symptoms can include fatigue, muscle aches, muscle spasms, tingling of the skin, weakness, and nerve pain. The medication includes a combination including low dose naltrexone, coenzyme Q, and vitamins B12 and B6. The treatment includes providing the medication at least once per day, and can be administered in any convenient manner including ingestion as a pill or capsule.

In a broad aspect, the medication comprises about 1-10 mg naltrexone, at least about 20 μg vitamin B12, at least about 5 mg vitamin B6, and at least about 2 mg coenzyme Q. Preferably, the medication also comprises at least one ancillary medication selected from a group consisting of an anticonvulsant, muscle relaxant, anxiolytic, demyelinating inhibitor, and a stimulant. Ancillary medications can include, for example, diazepam, cyclcobenzaprine, clonazepam, alprazolam, 9-tetrahydrocannibinol, fumarate, caffeine, and combinations thereof.

The medication and treatment can reduce the progression of MS, but does not include an immuno-suppressor and does not promote the formation of antibodies. The medication and treatment can be administered orally, and decreases physical symptoms such as, for example, fatigue, gait problems, visual dysfunction, and pain, and can also improve cognitive skills.

DETAILED DESCRIPTION OF THE INVENTION

Traditional treatments for MS have been only marginally effective at reducing the progression of the disease and do little to reverse symptoms. Additionally, traditional immuno-suppression therapy can render the person susceptible to other diseases such as cancer and contagious illnesses. Eventually, traditional treatments stimulate the production of antibodies that negate any further benefit.

Naltrexone is an opioid antagonist that has been approved by the U.S. Food and Drug Administration (FDA) for the treatment of addictions to opioids and alcohol. Low Dose Naltrexone (LDN) has been used as a treatment for a variety of diseases, including various types of cancers, HIV/AIDS, Parkinson's disease, Alzheimer's disease, amyotrophic lateral sclerosis (ALS), emphysema, as well as MS and other autoimmune diseases. LDN stimulates the production of endorphins, which are not only natural painkillers but important immune-modulators. Endorphin levels have been shown to be low in MS and other autoimmune and immuno-suppressive diseases.

When used in MS patients, LDN appears to modulate the immune system and promote healing. In contrast, high dose naltrexone exacerbates symptoms. Unlike other MS medications, LDN is substantially not immuno-suppressive and, unlike immunosuppressants, is not expected to increase the risk of infections and cancer. Without intending to be bound by this explanation, LDN may suppresses T cell proliferation and reduce the number of lymphocytes primed to target myelin/oligodendrocyte glycoprotein (MOG) the primary myelin antigen targeted in MS, thereby suppressing disease progression. Patients using LDN have reported improved quality of life, particularly mental abilities, and pain reduction. LDN alone has shown no improvement of physical ability other than to slow the progression of the disease.

The medication and treatment of the present invention include a combination of LDN, vitamins B12 and B6, coenzyme Q, and optionally one or more ancillary medications. In one embodiment of the treatment, the medication can be ingested. Antibodies have not been observed in response to the medication or treatment. Naltrexone is commonly marketed as the hydrochloride salt and hydrobromide salt. Vitamins B12 and B6 affect nervous system function. Vitamin B12 can affect the myelination of nerve cells, and exists in various forms but can conveniently be supplied as the synthetic vitamin, cyanocobalamin. Vitamin B6 benefits peripheral nerves and increases production of serotonin, a neurotransmitter. Coenzyme Q is an oil soluble vitamin-like substance, and is a component of the electron transport chain and aerobic cellular respiration. It participates in the production of ATP, which generates the vast majority of the body's energy. The medication and treatment include a combination of chemicals that synergistically reduce and even reverse the progression of MS, such as associated fatigue, muscle aches and spasms, weakness, and nerve pain. The medication and treatment has also shown benefit in the treatment of other diseases with similar symptoms, such as, for example, fibromyalgia, depression, and auto-immune and immuno-suppressive diseases.

Ancillary medications can include anticonvulsants, muscle relaxants, anxiolytics, demyelinating inhibitors, stimulants, and combinations thereof. For example, ancillary medications can include, diazepam, cyclcobenzaprine, clonazepam, alprazolam, 9-tetrahydrocannibinol (THC), fumarate, caffeine, and combinations thereof. The type and quantity of ancillary medication can be adjusted based on the symptoms of a particular person. Diazepam, also known as Valium®, is an anticonvulsant and can reduce muscle spasms. Cyclobenzaprine, also known as Flexeril®, is a skeletal muscle relaxant. Clonazepam, also known as Klonopin®, is an anticonvulsant and muscle relaxant. Alprazolam, also known as Xanax®, is an anxiolytic. THC can decrease neuropathic pain and spasticity. Fumarate includes any biologically active compound based on fumaric acid, $HO_2CCH=CHCO_2H$, including but not limited to salts and esters of fumaric acid. Fumarate is an intermediate in the citric acid cycle and is used by cells to produce energy in the form of adenosine triphosphate (ATP). Fumarate has also been linked to the preservation of myelin in the central nervous system, that is, oligodentrocites around nerve axons. U.S. Pat. No. 5,434,166 to Galsebrook entitled, Methods of Inhibiting Demylelinating and desmyelinating Diseases, is hereby incorporated by reference. Caffeine is a stimulant that does not harm oligodentrocites.

The medication and treatment should include sufficient levels of ingredients for pharmacological effect. An excess of naltrexone can actually exacerbate symptoms. An effective dose is from about 1-10 mg naltrexone, and more preferably from about 2-5 mg naltrexone. The medication and treatment will include at least about 20 μg of vitamin B12 and preferably at least about 40 μg of vitamin B12. The medication and treatment will also include at least about 5 mg vitamin B6 and at least about 2 mg coenzyme Q, with preferred ranges of at least about 10 mg and 5 mg, respectively. In addition to the LDN, vitamins and coenzyme, the treatment will also include the ancillary medication. The type and amount of ancillary medication will vary with the person. For example, anxiety can be affected with alprazolam, and clonazepam can reduce muscle spasms.

A typical medication and treatment can include a base composition comprising, for example, 50 μg B12, 20 mg B6, 10 mg Coenzyme Q, and 2-4 mg naltrexone (the "Base Composition"). Table 1 shows formulations A through R, which include the Base Composition and various ancillary medications. The treatment is typically administered as a pill or tablet once or twice daily. Treatments with lower levels of naltrexone are often given twice daily and higher levels of naltrexone can be given once daily.

Ancillary medications will be administered at clinically effective dosing levels. The dosing level must be sufficient to produce an effect but not so high as to promote toxicity. The specific formulation can be adjusted based on the patient and the patient's symptoms. For example, suitable ranges of ancillary medications can include:

a. Diazepam from about 0.05 mg to about 50 mg;
b. Cyclobenzaprine from about 0.5 mg to about 10 mg;
c. Clonazepam from about 0.1 mg to about 2 mg;
d. Alprazolam from about 0.05 mg to about 5 mg;
e. THC from about 0.1 μg to about 5 μg;
f. Fumarate from about 20 mg to about 800 mg; and
g. Caffeine from about 10 mg to about 200 mg.

Example 1

Patient A was a 41 year old female, who was diagnosed with MS 14 months previously based on an MRI of her brain and a lumbar puncture. She presented with gait difficulties, muscle spasms in the lower extremities, and short term memory dysfunction. Patient A had received injections of Avonex, a standard MS medication, with no improvement. Patient A was given a daily tablet of the medication comprising 3 mg naltrexone hydrochloride, 0.5 mg clonazepam, 100 μg vitamin B12 as cyanocobalamin, 20 mg vitamin B6, and 10 mg coenzyme Q. Patient A showed a 30% improvement in mental function as measured by the Mini Mental Status examination and an improvement in gait.

Example 2

Patient B was a 27 year old female, who was diagnosed 9 months previously with MS following an MRI of her brain and a lumbar puncture. Patient B experienced neuralgia pain in her left upper extremities at an 8-9 on a 10 point scale, and numbness in her left torso. Patient B had received Copaxone as a daily subcutaneous injection, but showed no decrease in her symptoms. Patient B was given a twice daily tablet of the medication comprising 2 mg naltrexone hydrochloride, 0.5 mg clonazepam, 100 μg vitamin B12 as cyanocobalamin, 20 mg vitamin B6, and 10 mg coenzyme Q. After six weeks, the pain in Patient B's left extremity had reduced to 1-3 on a 10 point scale, and her numbness had been eliminated.

TABLE 1

| Sample | Diazepam mg | Cyclobenzaprine mg | Clonazepam mg | Alprazolam mg | THC μg | Fumarate Mg | Caffiene mg |
|---|---|---|---|---|---|---|---|
| A | 0.25 | | | | | | |
| B | 0.25 | | | | | 120 | 20 |
| C | 0.10 | | | | | | |
| D | | 1.0 | | | | | |
| E | | 1.0 | | | | 120 | 20 |
| F | | | 0.25 | | | | |
| G | | | 0.25 | | | 120 | 20 |
| H | | | 0.10 | | | | |
| I | | | 0.05 | | | | |
| J | | | | 0.25 | | | |
| K | | | | 0.25 | | 120 | 20 |
| L | | | | 0.10 | | | |
| M | | | | 0.05 | | | |
| N | | | | | 2.0 | | |
| O | | | | | 2.0 | 120 | 20 |
| P | | | | | 1.0 | | |
| Q | | | | 0.1 | 0.5 | | |
| R | | | | 0.1 | 0.5 | 120 | 20 |

Example 3

Patient C was a 50 year old female, who had had MS for seven years. Diagnosis was confirmed by an MRI of her brain, lumbar puncture, and visual evolved response. Patient C experienced numbness on her right side, severe fatigue, generalized muscle spasms, and neuralgia pain of 5-6 on a 10 point scale. Patient C had been treated with Avonex with minimal improvement. Patient C had also been treated with low dose naltrexone of 3 mg daily with no improvement. For six weeks, Patient C was given a twice daily tablet of the medication comprising 2 mg naltrexone hydrochloride, 0.5 mg clonazepam, 100 µg vitamin B12 as cyanocobalamin, 20 mg vitamin B6, and 10 mg coenzyme Q. Patient C experienced substantial elimination (about 80%) of the numbness on her right side, reduction in pain to only 2-3 on a 10 point scale, decreased fatigue, and diminishment of muscle spasms by about 60%.

Numerous modifications and variations of the present invention are possible. It is, therefore, to be understood that within the scope of the following claims, the invention may be practiced otherwise than as specifically described. While this invention has been described with respect to certain preferred embodiments, different variations, modifications, and additions to the invention will become evident to persons of ordinary skill in the art. All such modifications, variations, and additions are intended to be encompassed within the scope of this patent, which is limited only by the claims appended hereto.

The invention claimed is:

1. A medication for treating disease consisting of 1 mg to about 10 mg naltrexone, at least about 2 mg coenzyme Q, at least about 20 µg vitamin B12, at least about 5 mg vitamin B6, and from about 0.5 to about 10 mg cyclobenzaprine.

* * * * *